United States Patent [19]

Cawood

[11] Patent Number: 4,759,348

[45] Date of Patent: Jul. 26, 1988

[54] ENDOSCOPE ASSEMBLY AND SURGICAL INSTRUMENT FOR USE THEREWITH

[76] Inventor: Charles D. Cawood, 11527 N. Lou Al Ct., Houston, Tex. 77024

[21] Appl. No.: 306,086

[22] Filed: Sep. 28, 1981

[51] Int. Cl.$^4$ ............................................. A61B 1/06
[52] U.S. Cl. ........................................ 128/6; 128/321
[58] Field of Search ................... 128/4, 6, 328, 346, 128/349 R, 7-9, 303.15, 321; 248/106, 117.4

[56] References Cited

U.S. PATENT DOCUMENTS

| | | | |
|---|---|---|---|
| 1,959,127 | 5/1934 | Duerme | 128/6 |
| 2,238,660 | 4/1941 | Santori | 128/346 |
| 2,583,937 | 1/1952 | Fossati | 128/303.15 |
| 2,691,370 | 10/1954 | Wallace | 128/6 |
| 2,990,765 | 7/1961 | Winzenburg | 128/6 |
| 3,173,414 | 3/1965 | Guillant | 128/8 |
| 3,316,910 | 5/1967 | Davis | 128/328 |
| 3,413,976 | 12/1968 | Roze | 128/328 |
| 3,726,272 | 4/1973 | Fukami et al. | 128/6 |
| 3,858,577 | 1/1975 | Bass et al. | 128/8 |
| 3,960,143 | 6/1976 | Terada | 128/4 |
| 4,043,323 | 8/1977 | Komiya | 128/4 |
| 4,043,343 | 8/1977 | Williams | 128/321 |
| 4,046,149 | 9/1977 | Komiya | 128/328 |
| 4,046,150 | 9/1977 | Schwartz et al. | 128/328 |
| 4,102,333 | 7/1978 | Storz | 128/6 |
| 4,369,768 | 1/1983 | Vukovic | 128/6 |

FOREIGN PATENT DOCUMENTS

| | | | |
|---|---|---|---|
| 2315056 | 10/1974 | Fed. Rep. of Germany | 128/4 |
| 440731 | 7/1912 | France | 128/349 R |
| 285317 | 5/1931 | Italy | 248/117.4 |
| 446123 | 4/1936 | United Kingdom | 248/106 |

OTHER PUBLICATIONS

Tsuchida, S., A New Operative Fiberpyeloscope, Journal of Urology, 117:643-5 (May 1977).
Olinger, C. P. & R. L. Ohlhaber, Eighteen-Guage Needle Endoscope with Flexible Viewing System, Surg. Nurol., 4:537-8 (1975).
Stotter, L., H. J. Wiendl & B. Ultsch, An Improved Flexible Cholangioscope, Endoscopy, 7:150-3 (1975).
Gittes, R. F., Operative Nephroscopy, Journal of Urology, 116:148-52 (1976).
Miki, M., Y. Inaba & T. Machida, Operative Nephroscopy with Fiberoptic Scope: Preliminary Report, Journal of Urology, 119:166-8 (Feb. 1978).

Primary Examiner—Max Hindenburg
Attorney, Agent, or Firm—Tilton, Fallon, Lungmus & Chestnut

[57] ABSTRACT

An endoscope assembly, and the surgical instrument associated with it, capable of providing superior visibility of an operative site while at the same time insuring the transmission of tactile information to the surgeon through the handle of the instrument. The endoscope assembly comprises an optical head equipped with a connector or connectors for externally and releasably attaching the head to a surgical instrument at the neck portion adjacent the operating end thereof, an eyepiece or other viewing unit remote from the head, and an elongated flexible cable extending between the two. In the embodiment disclosed, the cable contains a light-transmitting waveguide for illuminating the operative area and a fiberoptic bundle for transmitting a coherent image of the area so illuminated. The cable may also be provided with a passage for delivering irrigating fluid (liquid or gas) to the operative site.

25 Claims, 1 Drawing Sheet

U.S. Patent
Jul. 26, 1988
4,759,348
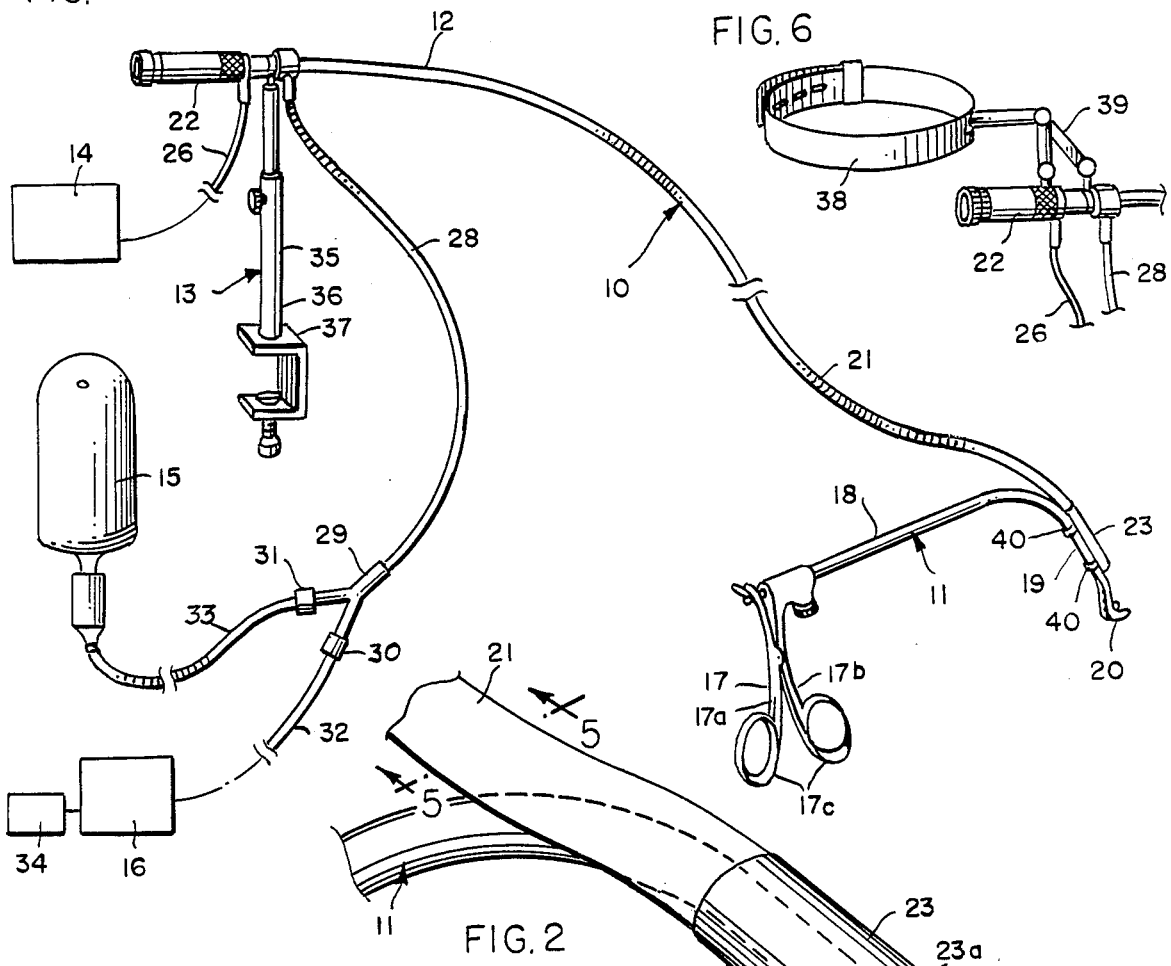
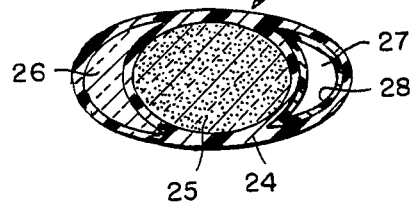
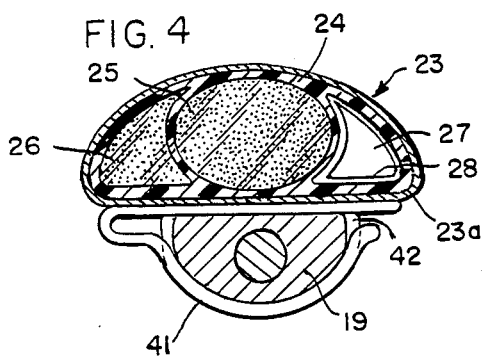
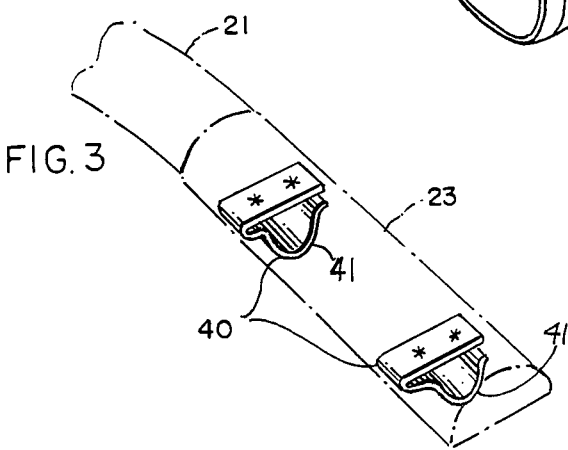

ENDOSCOPE ASSEMBLY AND SURGICAL INSTRUMENT FOR USE THEREWITH

BACKGROUND AND SUMMARY

Various types of specialized forceps, clamps, and other surgical instruments have been developed over the years for use in performing specific surgical operations, and in many cases the configuration and construction of such instruments has been based not only on anatomical considerations but also on the importance of providing the surgeon with tactile information essential in achieving proper control over such an instrument. Thus, forceps used for removal of kidney stones generally have angular shank portions of minimal length so that the closed jaws of such an instrument can be readily inserted into the kidney through an incision in the renal pelvis, and the tips of the closed jaws may then be used as a probe to help the surgeon locate the stones requiring removal. Visual aids such as fluoroscopy and x-radiography are often used, but a surgeon manipulating such an instrument must nevertheless rely primarily on tactile sensitivity to locate, grasp, and remove the calculi.

More recently, endoscopic instruments have been developed to provide surgeons with an internal view of the organ or body passage requiring treatment, such endoscopes typically having channels through which a miniaturized forceps, commonly called flexible instruments, are inserted and advanced. While such a system does provide the surgeon with an internal view of the operative site, miniaturization reduces the effectiveness of the flexible instrument for many functions such as, for example, grasping and removing larger size kidney stones. Moreover, the flexibility of the grasping (or cutting) instrument, and the distance between its jaws and the remote handles held by the surgeon, all but eliminate the transmission of tactile signals and require that almost complete reliance be placed on endoscopic observation in performing surgical manipulations. Not only are the surgeon's hands spaced well away from the distal end of the endoscope and the jaws of the instrument, but they are normally fully occupied by the manipulations required at the proximal end of the equipment. One hand is commonly used to hold and direct the endoscope while the other is used to direct and operate the flexible instrument and also to control the irrigation system—all such manipulations occurring at the proximal end of the endoscopic system, well away from the organ or body part undergoing surgical treatment. Any tactile feedback is minimal because of the lack of rigidity of the instrument and the distance between its jaws and operating controls.

References illustrative of the state of the art are U.S. Pat. Nos. 3,960,143, 4,046,149, 4,046,150, 4,043,323, and 3,413,976. Other publications are Tsuchida, S., A New Operative Fiberpyeloscope, Journal of Urology, 117:643-5 (May 1977), Olinger, C. P. & R. L. Ohlhaber, Eighteen-Guage Needle Endoscope with Flexible Viewing System, Surg. Neurol. 4:537-8 (1975), Stotter, L., H. J. Wiendl, & B. Ultsch, An Improved Flexible Cholangioscope, Endoscopy 7:150-3 (1975), Gittes, R. S., Operative Nephroscopy, Journal of Urology, 116:148-52 (1976), Miki, M., Y. Inaba, & T. Machida, Operative Nephroscopy with Fiberoptic Scope: Preliminary Report, Journal of Urology, 119:166-8 (February 1978).

An object of this invention therefore lies in providing an endoscope assembly and surgical instrument which allow a surgeon to use both hands at the surgical site, thereby providing maximum tactile input through hand contact with the organ and the surgical instrument used to enter that organ, while at the same time providing endoscopic visualization of the interior of the organ and the tip action of the instrument involved. A further object is to provide a system which allows a surgeon to use an instrument having greater holding capacity and effectiveness than a miniaturized intraluminal grasping instrument, and which also provides the surgeon with both tactile input and visual confirmation. Another object is to provide an endoscopic attachment for a rigid surgical instrument having jaws for probing, grasping, and/or cutting, the attachment being removable when not needed, or when its use is required with another related type of instrument. A still further object is to provide a low profile endoscopic attachment which contains flexible transmitting means for illuminating and transmitting images, and which also provides a passage for irrigation of the operative site.

In brief, the instrument used in the combination of this invention may be any of a variety of specialized instruments used for probing and grasping or, in some cases, cutting, which are designed to be held and operated by one hand and which provide the surgeon with a high level of tactile input. For that purpose, such an instrument should have a handle or shank portion of rigid construction. For example, where the instrument is to be used for nephrolithotomy or phelolithotomy with calyceal stone extraction, the instrument may be a modified version of conventional Ray or Randall forceps. Such instruments are rigid enough to be precisely manipulated by the surgeon's hand in close proximity to the kidney (preferably with the other hand holding and manipulating the kidney), while providing maximum tactile sensitivity and sufficiently greater capability for grasping and removing larger stones (those having a diameter greater than about 0.8 centimeters) as well as stones of smaller size.

The endoscope assembly includes an elongated flexible cable equipped at one end with an eyepiece or other viewing means and at the other with an optical head. Only the head is directly and externally connected to the instrument, such rigid connection being made to the instrument's neck portion adjacent the jaws thereof. The cable transmits images or image-producing signals from the illuminated operative site at the head back to the viewing means so that the surgeon will have visual confirmation of the action of the instrument's working end as well as direct tactile input transmitted through the rigid handle or shank of the hand-held instrument.

In the particular embodiment disclosed, the connection between the optical head and the instrument is releasable, the head being equipped with one or more spring clips for detachably engaging the instrument's neck portion. The head is generally crescent-shaped in cross section so that its contour complements that of the instrument. A coherent optic bundle extends from the head and through the flexible cable to the eyepiece for providing the surgeon with visual confirmation of the instrument's tip or jaw action which, as already indicated, is also confirmed by direct tactile input. The illuminating means may take the form of a ligh-transmitting waveguide extending through the cable to illuminate the operative area, such waveguide being connected at its proximal end to a suitable high-intensity light source. Ideally, the cable also provides a flow passage for the delivery of fluid (liquid or gas) for irrigation or other purposes, the flow passage and the illuminating means being disposed on opposite sides of the coherent image-transmitting waveguide.

A support is provided for holding the eyepiece so that the surgeon's hands are free to remain near the operative site at the distal end of the instrument. The support may take the form of a standard adapted to be mounted upon a floor, table, or other stationary surface, or a headband worn by the surgeon.

Other features, objects, and advantages of the invention will become apparent from the specification and drawings.

DRAWINGS

FIG. 1 is a perspective view, shown partly diagrammatically, depicting the complete system of an embodiment of this invention.

FIG. 2 is an enlarged fragmentary perspective view showing the distal ends of the instrument and endoscope assembly.

FIG. 3 is a perspective view of the distal end of the endoscope assembly in the same position illustrated in FIG. 2, but with the head and cable being shown in phantom to illustrate a clip construction for securing the endoscope to the neck of a surgical instrument.

FIG. 4 is an enlarged cross sectional view taken along line 4—4 of FIG. 2.

FIG. 5 is an enlarged cross sectional view along line 5—5 of FIG. 2.

FIG. 6 is a fragmentary perspective view illustrating alternative support means for holding the eyepiece of the endoscope assembly in operation position.

DETAILED DESCRIPTION OF PREFERRED EMBODIMENT

Referring to the drawings, the numeral 10 generally designates a complete operating system comprising a hand-holdable surgical instrument 11, an endoscope assembly 12, support means 13 for the eyepiece of that assembly, a light source 14, and one or more sources 15 and 16 of irrigating fluid.

The instrument 11 includes a handle portion 17 dimensioned and constructed to be held and operated by one hand, a rigid shank portion 18 which extends a limited distance from the handle and which, in the embodiment illustrated, is curved near its distal end, a neck portion 19 which may constitute a distal extension of the shank portion, and jaws 20 operatively connected to the operating elements of handle portion 17 and adapted to open and close when the elements of the handle portion are manipulated. In its general outline and construction, the particular instrument 11 illustrated in the drawings is essentially a modified version of a forceps commonly known as a Ray kidney stone forceps, although it will be understood that for other types of surgery the instrument 11 may assume a substantially different appearance. It is believed essential, however, that regardless of the configuration and intended use of the instrument, such instrument must be small enough to be held and operated by one hand, have an operating end normally provided with jaws for grasping and/or cutting, and be rigid enough to provide the surgeon with positive tactile feedback in use.

Handle portion 17 is shown having a pair of lever elements 17a and 17b equipped with finger loops 17c. While such an arrangement has been found effective for purposes of instrument manipulation and control, other arrangements may be substituted. For example, a handle composed of a pair of reciprocable elements, as generally disclosed in certain of the aforementioned patents, may also be effectively used.

Endoscope assembly 12 includes an elongated flexible cable 21 equipped at its proximal end with eyepiece 22 and at its distal end with optical head 23. The cable 21 has a sheath 24 formed of any suitable resilient and flexible polymeric material through which flexible transmitting means 25 and 26 extend. One such means 26 transmits energy from source 14 to the head 23 for illuminating the site of surgical treatment. The other transmitting means 25 transmits images or image-producing signals from head 23 to the viewing means (eyepiece) 22.

In the embodiment illustrated, the transmitting means 25 comprises a coherent bundle of glass fibers capable of transmitting an image from the operative site to the viewer, although it is conceivable that such means might take other forms such as, for example, a flexible conductive lead for transmitting electrical signals from a receiver or scanner in the head to the viewing means where such signals are then processed to produce the visual images. Similarly, while illuminating means 26 is depicted and described herein as a fiberoptic bundle, it might take the form of a flexible electrical conductor acting in combination with a head-mounted lamp or other illuminating device, or a waveguide consisting essentially of a single light-transmitting fiber or tube.

In the preferred embodiment shown in the drawings, the flexible cable is of rounded or oval cross section and the image-transmitting bundle 25 extends through that cable along the central axis thereof. The illuminating bundle or waveguide 26 may be of smaller cross sectional area than the image-transmitting bundle and may be disposed alongside the latter, in which case the illuminating bundle 26 may be crescent-shaped in cross section (FIG. 5).

The flexible sheath 24 of the cable may also include a flow passage 27 extending along that side of the coherent fiberoptic cable 25 opposite from the illuminating cable 26 (FIG. 5). The flow passage may be defined by an inner protective flexible tube 28 which extends through the cable and which exits therefrom at or near eyepiece 22. As shown in FIG. 1, tube 28 may extend to a branched coupling 29 equipped with check valves 30 and 31. One of the branches may lead through hose 32 to a pulsatile source of irrigating fluid 16, whereas the other branch may lead through hose 33 to a suspended bag 15 which serves as a non-pulsating fluid source. A manually-operated valve (not shown) may be provided in line 33 to control fluid flow, it being understood that during an operative procedure a continuous flow at low pressure is normally required for internal viewing. When pulsatile flow is needed, source 16, which may be driven by an electric vibrator in a manner well known in the art in connection with oral hygiene irrigating devices, may be activated and deactivated by a suitable foot controller 34. The pulsatile flow from source 16 is intended to be used for clearing away any tissue particles, blood, or other matter to prevent obscuring of the view through eyepiece 22 and/or for dislodging small particles from the organ's interior (such as stone particles within the calyces of the kidney).

The viewing means or eyepiece 22 shown in FIG. 1 is mounted upon support means 13 in the form of a standard 35 adapted to be secured at its lower end 36 to a table, floor, or other stationary support surface. The standard should be capable of telescoping, and should be provided with a pivotal connector at its upper end, to permit vertical and angular adjustment of the eyepiece. The base 37 of the standard may take the form of a clamp, suction cup assembly or tripod leg construction, all as known in the art.

The standard-equipped support 13 represents a preferred construction because it may be used to locate the eyepiece 22 in any suitable position selected by the surgeon while still readily permitting the surgeon to look away from the eyepiece when direct viewing of the operative site, or instrument 11, or any other object or person, is required. However, it has also been found effective to provide support means in the form of a headband 38 and connector 39 as depicted in FIG. 6. The connector 39 is secured to both the headband and eyepiece 22 and is adjustable to facilitate positioning of the eyepiece directly in front of the wearer's eye. Band 38 may also be adjustable as indicated in FIG. 6.

Head 23 is an extension of cable 21 and contains extended portions of fiberoptic bundles 25 and 26 as well as of irrigation tube 28. Objective lens 25a is mounted at the extreme distal end of bundle 25 and, if desired, a similar lens 26a may be provided at the distal end of bundle 26, the latter being more useful for preventing fluids from invading bundle 26 than for optical purposes. A protective casing 23a formed of rigid material may extend about the head, not only to prevent damage to the optics encased within the head but also to provide a secure attachment for one or more attachment clips 40.

Referring to FIGS. 3 and 4, it will be observed that a pair of spring clips 40 are secured to the underside of head casing 23a and are provided with arcuate spring arms which receive the neck portion 19 of instrument 11. The straps or arms 41 of the clips are received in peripheral grooves or channels 42 that, as indicated in FIG. 4, extend about at least the underside the neck portion 19 to secure head 23 against longitudinal sliding movement along the neck and to assist the user in properly positioning the head when endoscope 12 is to be coupled to instrument 11. To insure a rigid but releasable interconnection between head 23 and instrument 11, a pair of longitudinally-spaced clips 40 are shown in the drawings; however, it is to be understood that a greater or smaller number of such clips may be suitable for purposes of this invention.

In the operation of this system as, for example, in the case of kidney stone removal, a surgeon may find that a number of different instruments 11, all of the same general construction but with different shank curvatures, will be necessary in order to enter different calyces for stone detection and removal. In that event, head 23 may be readily detached from one instrument and clipped to the neck of another instrument of different curvature. Furthermore, in certain instances where the surgeon concludes that visual verification through an endoscope is unnecessary, and where tactile input and external observation are sufficient, the endoscope 12 may be completely disconnected and at least temporarily laid aside.

While the scope assembly 12 has been described in conjunction with surgical instruments, it is believed evident that such assembly might be adapted for use with any essentially rigid hand-held instrument that must be oriented and manipulated under conditions which require the operator to receive and respond to tactile signals transmitted through the instrument itself and which, because of the nature of the operation, prevent the operator from directly viewing the working end of the instrument and the operative site. Under such circumstances, the rigidity of the instrument, and the fact that it is hand held, allow the instrument to function as an extension of the hand and to be oriented, steered, and manipulated in part through tactile sensations which yield a perception of the action of the instrument in the "mind's eye" of the user. The visual input provided by the scope assembly 12 serves to confirm and supplement such tactile input to give the operator greater control over the operation of the instrument, whether it be in a surgical or non-surgical procedure.

While in the foregoing I have disclosed an embodiment of the invention in considerable detail for purposes of illustration, it will be understood by those skilled in the art that many of these details may be varied without departing from the spirit and scope of the invention.

I claim:

1. In combination with a surgical instrument dimensioned and adapted to be held and operated by one hand; said instrument having non-flexible handle, shank, and operating end portions rigidly connected to each other to provide tactile feedback therethrough to a user gripping and manipulating said handle portion when objects are engaged by said operating end portion; an image-receiving assembly comprising an optical head, viewing means remote from said head, and an elongated flexible cable assembly extending therebetween; mounting means rigidly but detachably securing said head externally to said operating end portion of said instrument; said instrument and said viewing mean being independently movable in relation to each other to the extent permitted by said flexible cable assembly; said cable assembly including first flexible transmitting means extending therethrough for transmitting energy to said head for illuminating a working area adjacent said operating end portion; and second flexible transmitting means extending through said cable from said head to said viewing means for providing at said viewing means an image of the work area illuminated by said first transmitting means adjacent said operating end portion.

2. The combination of claim 1 in which said mounting means comprises at least one spring clip.

3. The combination of claim 1 in which said mounting means comprises a pair of spring clips spaced longitudinally apart along said head.

4. The combination of claims 2 or 3 in which each spring clip is mounted upon said head and releasably embraces said operating end portion of said instrument.

5. The combination of claim 4 in which said operating end portion of said instrument is peripherally grooved to receive said clips and to anchor said end portion and head against relative longitudinal sliding movement.

6. The combination of claim 1 in which said head is generally crescent-shaped in transverse section.

7. The combination of claim 6 in which said second flexible transmitting means comprises a coherent image-transmitting fiberoptic bundle extending through said head along the longitudinal symmetrical midplane thereof.

8. The combination of claim 7 in which said first flexible transmitting means comprises a light-conducting wave-guide extending through said head along one side of said second bundle.

9. The combination of claim 8 in which an irrigation passage extends through said cable assembly for delivering irrigating fluid through said head to a work area, said irrigating passage extending through said head along the side of said image-transmitting fiberoptic bundle opposite from said light-transmitting waveguide.

10. In combination with a surgical instrument dimensioned and adapted to be held and operated by one hand; said instrument having non-flexible handle, shank, and operating end portions rigidly connected to each other to provide tactile feedback therethrough to a user gripping and manipulating said handle portion when objects are engaged by said operating end portion; a scope assembly comprising a generally rigid head portion, viewing means remote from said head portion, and an elongated flexible cable assembly extending between said head portion and said viewing means; connecting means detachably but rigidly securing said head portion alongside said operating end portion of said instrument; said instrument and viewing means being independently movable in relation to each other to the extent permitted by said flexible cable assembly; said scope assembly including a fiberoptic waveguide extending through said cable assembly for transmitting light to said head portion for illuminating a work area adjacent the operating end portion of said instrument; and a fiberoptic bundle of oriented fibers extending through said cable from said head portion to said viewing means for transmitting a coherent image of the work area illuminated by said waveguide; and support means for supporting said viewing means for viewing the image of the illuminated work area by a user.

11. The combination of claim 10 in which said connecting means comprises at least one spring clip mounted upon said head portion and releasably engaging the operating end portion of said instrument.

12. The combination of claim 11 in which said operating end portion of said instrument is peripherally grooved to receive said clip and to lock said end portion of said instrument and said head portion of said scope against relative longitudinal sliding movement.

13. The combination of claim 10 in which said head is generally crescent-shaped in transverse section.

14. The combination of claim 13 in which said fiberoptic bundle extends through said head portion along the longitudinal midplane of symmetry thereof.

15. The combination of claim 14 in which said waveguide extends through said head portion along one side of said fiberoptic bundle.

16. The combination of claim 15 in which an irrigation passage extends through said scope assembly for delivering irrigating fluid through said head portion to a work area, said irrigating passage extending through said head portion along the side of said fiberoptic bundle opposite from said waveguide.

17. The combination of claim 10 in which said support means comprises a standard connected at its upper end to said viewing means and equipped at its lower end with means for engaging a stationary support surface.

18. The combination of claim 10 in which said viewing means comprises an eyepiece and said support means comprises a headband adapted to be worn by a user and equipped with means for retaining said eyepiece.

19. The combination of claims 1 or 10 in which said operating end portion of said instrument includes a pair of jaws operatively connected through said shank portion to said handle portion of said instrument.

20. An endoscopic attachment for use with a surgical instrument dimensioned and adapted to be held and operated by one hand; said instrument having non-flexible handle, shank, and operating end protions rigidly connected to each other to provide tactile feedback therethrough to a user gripping and manipulating said handle portion when objects are engaged by said operating end portion; said attachment comprising viewing means, an optical head remote from said viewing means, and an elongated flexible cable assembly extending therebetween; said cable assembly including first flexible transmitting means extending therethrough for transmitting light to said head for illuminating an operative site adjacent an operating end portion of a surgical instrument and a second flexible transmitting means extending through said cable from said head to said viewing means for transmitting an image of an operative site illuminated by said first transmitting means; coupling means for operatively connecting a light source to said first transmitting means; and spring clip means secured to said head for releasably, rigidly, and externally attaching said head to an operating end portion of a hand-held surgical instrument; said head including a rigid outer side casing; said spring clip means being secured to said casing and including a spring arm extending generally transversely with respect to said head for flexing movement in a generally transverse plane.

21. The attachment of claim 20 in which said head is elongated and generally crescent-shaped in cross section, having a convex top surface and a generally flat undersurface; said spring clip means being secured to said head along said undersurface.

22. The attachment of claim 21 in which said spring clip means comprises a pair of spring clips spaced longitudinally apart with respect to said head along the undersurface thereof.

23. The attachment of claim 21 in which said second transmitting means extends through said head along the longitudinal midplane of symmetry thereof.

24. The attachment of claim 23 in which said first transmitting means extends through said head along one side of said second transmitting means.

25. The attachment of claim 24 in which an irrigation passage extends through said cable assembly and head for delivering irrigating fluid to an operative site, said irrigating passage extending through said head along the side of said second transmitting means opposite from said first transmitting means.

* * * * *